United States Patent [19]

Vanlergerghe et al.

[11] 3,959,460

[45] *May 25, 1976

[54] COSMETIC COMPOSITIONS CONTAINING ANIONIC SURFACE ACTIVE AGENT CONTAINING MONO- OR POLYHYDROXYLATED MONO- OR POLY ETHER CHAINS AND A TERMINAL ACID GROUP

[75] Inventors: Guy Vanlergerghe, Claye-Souilly; Henri Sebag, Paris, both of France

[73] Assignee: L'Oreal, Paris, France

[ * ] Notice: The portion of the term of this patent subsequent to July 2, 1991, has been disclaimed.

[22] Filed: May 1, 1974

[21] Appl. No.: 466,060

Related U.S. Application Data

[63] Continuation-in-part of Ser. No. 264,864, April 21, 1972, Pat. No. 3,822,346, which is a continuation of Ser. No. 749,580, Aug. 2, 1968, abandoned.

[30] Foreign Application Priority Data

Aug. 7, 1967  Luxemburg............................ 54263

[52] U.S. Cl.................................. 424/70; 424/317; 424/365; 260/535 R; 252/356; 8/10.1; 252/545
[51] Int. Cl.².......................................... A61K 7/00
[58] Field of Search ............. 424/317, 70; 260/535; 252/356

[56] References Cited
UNITED STATES PATENTS

| | | | |
|---|---|---|---|
| 2,111,820 | 3/1938 | Skindorff et al................ | 253/356 X |
| 2,183,853 | 12/1939 | Hausmann et al............. | 260/535 X |
| 2,623,900 | 12/1952 | Hofer............................. | 260/535 X |
| 2,745,857 | 5/1956 | Britton et al.................... | 260/535 X |
| 3,427,248 | 2/1969 | Lamberti et al................. | 252/117 |

*Primary Examiner*—Mayer Weinblatt
*Assistant Examiner*—Charles R. Wolfe, Jr.
*Attorney, Agent, or Firm*—Cushman, Darby & Cushman

[57] ABSTRACT

A cosmetic composition comprises an aqueous solution of an anionic surface active agent selected from the group consisting of (a) a surface active agent of the formula

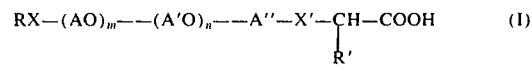

$$RX-(AO)_m---(A'O)_n---A''-X'-\underset{R'}{CH}-COOH \qquad (I)$$

wherein R is selected from the group consisting of alkyl and alkenyl, each having 8 to 22 carbon atoms and alkylphenyl having 12 to 22 carbon atoms;
X and X' are each selected from the group consisting of oxygen, sulfur and sulfoxide;
A is selected from the group consisting of ethylene, propylene and butylene;
A' is selected from the group consisting of $-C_2H_3(CH_2OH)-$ and $-CH_2CHOH-CH_2-$;
A'' is selected from the group consisting of $-CH_2CHOH-CH_2-$, $-CH_2CH_2CH_2-$ and $-CH_2CH(CH_3)-$ with the proviso that at least one of A' and A'' is hydroxyalkylene as set forth in the respective definitions of A' and A'' above;
m and n represent numbers having a statistical average value between 0 and 10 inclusive with the proviso that n is other than 0 when A'' is other than hydroxyalkylene and when m and n are both zero, X' is sulfoxide;
R' is selected from the group consisting of hydrogen and a lower alkyl having from 1–12 carbon atoms;
b. the magnesium salt of (a); and
c. the alkanolamine salt of (a), said surface active agent being present in amounts ranging from 0.1–20% by weight of said composition.

5 Claims, No Drawings

COSMETIC COMPOSITIONS CONTAINING ANIONIC SURFACE ACTIVE AGENT CONTAINING MONO- OR POLYHYDROXYLATED MONO- OR POLY ETHER CHAINS AND A TERMINAL ACID GROUP

This application is a continuation-in-part of our application Ser. No. 246,864, filed Apr. 21, 1972, now U.S. Pat. No. 3,822,346 which is a continuation of our application Ser. No. 749,580, filed Aug. 2, 1968, now abandoned.

This invention relates to an anionic chemical compound which is a surface active agent of the formula:

$$RX-(AO)_m-(A'O)_n-A''X'-\underset{R'}{CH}-COOH \qquad (I)$$

in which

R is aan alkyl or alkenyl aliphatic radical having 8 to 22 carbon atoms or an alkyl-aryl radical, having 12 to 22 carbon atoms on the alkyl group;

X and X' can be identical or different and represent oxygen, sulfur or a sulfoxide group;

A represents an ethylene, propylene or butylene radical;

A' represents $-C_2H_3(CH_2OH)-$ or $-CH_2CHOH-CH_2-$;

A'' represents $-CH_2CHOH-CH_2-$, $-CH_2CH_2CH_2-$ or $-CH_2CH(CH_3)-$;

at least one of the radicals A' and A'' being a hyroxyalkylene radical such as $-CH_2CHOH-CH_2-$ or $C_2H_3(CH_2OH)-$;

$m$ and $n$ each represent a number having a statistical average value between 0 and 10 inclusive;

R' represents a hydrogen atom or a lower alkyl radical containing 1 or 2 carbon atoms.

If $m$ and $n$ are both equal to O, X' must represent a sulfoxide group.

The present invention also includes the alkali metal (Na, K, etc.) and alkaline earth (Mg, Ca, etc.) salts, the ammonium salts, and the amine salts of carboxylic acids corresponding to formula I.

It should be noted that one of the essential features of the above-defined products is that they comprise a mono-, or polyether chain, either mono- or polyhydroxylated between the lipophilic portion of its molecule and the carboxylic acid group. This mono- or polyhydroxylated chain can be preceded by a polyoxyalkylene group. When a single $-CH_2CHOH-CH_2-$ radical is positioned between the lipophilic portion and the carboxylic group, it is accompanied, as indicaated in the above definition, either by a sulfoxide bond or at least one alkylene group.

The properties of the products according to the invention are in general similar to those of the polyoxyalkylene-carboxylic acids heretofore known, but they are clearly more accentuated. In particular, the compounds according to the invention have very valuable properties with respect to solubility. They dissolve readily in concentrated sodium hydroxide solutions because they contain the hydroxyalkylene radicals designated by A' and A''. They also disperse or dissolve readily in water, and can be used even in "hard" water. To be precise, the alkaline earth salts of the carboxylic acids of this invention will disperse or dissolve in water provided that in the above general formula, the parameter $n$ has a value equal to or greater than 0.5 when X is an atom of oxygen or sulfur. Finally these products are readily soluble in an acid medium and highly compatible with cationic surface active agents.

When the compounds of this invention are used in hard water, it should be noted that the above properties are completely unexpected, because the most closely similar compounds have no such properties. For example, when any of the known compounds $C_{12}H_{25}-S-CH_2-COONa$, $$C_{12}H_{25}-\underset{\underset{O}{\downarrow}}{S}-CH_2-COONa, \text{ and } C_{12}H_{25}-\underset{\underset{O}{\downarrow}}{S}-CH_2-CH_2-COONa$$

are dissolved in demineralized water at a concentration of 0.5% turbidity results when an 0.1% solution of calcium chloride is added, whereas the closely similar compound according to the invention, $$C_{12}H_{25}-OCH_2-CHOH-CH_2-\underset{\underset{O}{\downarrow}}{S}-CH_2COONa,$$

is subjected to the same test only very slight turbidity results from the addition of a quantity of calcium chloride about 100% in excess of the quantity theoretically required for double decomposition. Moreover, in this case, even the presence of a considerable excess of calcium ions, more than 10 times the equivalent quantity, the resulting dispersion is not opaque, whereas with the compounds heretofore known the turbidity progresses rapidly to complete opacity.

The compounds according to the invention have foaming and detergent properties and can be desirably used in shampoos. Their application to the hair imparts thereto a much softer touch than when alkyl sulfates are used. The compounds of this invention can also be used as a carrier for hair dyes which soften the hair.

More particularly, the present invention relates to a cosmetic composition comprising in an aqueous solution a surface active agent selected from the group consisting of a. a surface active agent of the formula $$RX-(AO)_m-(A'O)_n-A''-X'-\underset{R'}{CH}-COOH$$

wherein

R is selected from the group consisting of alkyl and alkenyl, each having 8–22 carbon atoms and alkyl phenyl selected from the group consisting of p-octyl phenyl, p-nonyl phenyl, p-dodecyl phenyl and p-hexadecyl phenyl;

X and X' are each selected from the group consisting of oxygen, sulfur and sulfoxide;

A is selected from the group consisting of ethylene, propylene and butylene;

A' is selected from the group consisting of $-C_2H_3(CH_2OH)-$ and $-CH_2CHOH-CH_2-$;

A'' is selected from the group consisting of $-CH_2CHOH-CH_2-$, $-CH_2CH_2CH_2-$ and $-CH_2CH(CH_3)$, with the proviso that at least one of A' and A'' is hydroxyalkylene as set forth in the respective definitions of A' and A'' above;

$m$ and $n$ represent numbers having a statistical average value between 0–10 inclusive, with the proviso that $n$ is other than 0 when $A''$ is other than hydroxyalkylene and when $m$ and $n$ are both equal to zero, $X'$ is sulfoxide; and R' is selected from the group consisting of hydrogen and alkyl having from 1–12 carbon atoms, b. the magnesium salt of (a); and c. the alkanolamine salt of (a), said surface active agent being present in amounts ranging from 0.1–20% by weight of said composition.

Preferably the alkanolamine employed to prepare the salt of (a) above is selected from the group consisting of 2-amino-2-methyl propanol, triethanolamine and 2-amino-2-methyl-1,3-propanediol.

Any known hair dye can be mixed with the surface active agents of this invention to form an improved dye product which colors and softens the hair. Preferred hair dyes to be used in such compositions include nitro amino phenyl hair dyes, quaternary ammonium anthraquinone hair dyes, azo hair dyes, etc.

Moreover, outside the cosmetic field, the compounds according to the invention can be utilized for many different purposes, in particular for degreasing wool and bleaching and mercerizing cotton.

In order to prepare the chemical compounds corresponding to formula (I) in which X' represents a thioether bond, a mercapto-alkane acid or a salt or low molecular weight ester of such an acid, is reacted with either:

a glycidol ether corresponding to the formula:

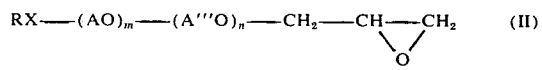

(II)

wherein

R, X, A, $m$ and $n$ have the significances hereinbefore indicated and

A''' is identical to A or represents either $C_2H_3(CH_2Cl)$ or $C_2H_3(CH_2Br)$;

or an allyl alcohol ether corresponding to the formula:

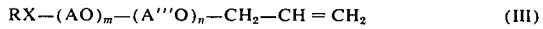

(III)

wherein R, X, A, A''', $m$ and $n$ have the significances hereinbefore assigned thereto.

When glycidyl ether corresponding to formula (II) is used, the esters or salts of the mercapto-alkanoic acid give the best results. The molar proportion of the mercapto-alkanoic acid, its salts and esters, to the glycidyl ether is of the order of 1 to 1.5 and preferably from 1 to 1.1 mols of the former per mol of the latter.

The glycidyl ethers are reacted with the esters or salts of the mercapto-alkanoic acids at a temperature between 20° and 150°C and preferably between 100° and 120°C. In order to obtain high yields in a relatively short time, alkaline catalysts such as alcoholates, mercaptides, hydroxides and tertiary amines can be used. Among the suitable tertiary amines are triethylamine, tripropylamine, 1,3-N-N'-tetramethylbutane-diamine and N-N'-tetramethylethylene-diamine. When these tertiary amines are used with esters of mercaptoalkanoic acids, thioethers corresponding to formula (I) are obtained, in the form of methyl or ethyl esters with practically quantiative yields. The tertiary amines used as catalysts preferably constitute from 1 to 5% of the reaction mixture.

When the radical A''' of formula (II) represents a halogenated radical and when esters of the mercaptoalkanoic acids are used, the resulting thioether is polyhalogenated, and in order to then obtain the product of formula (I), the halogen atoms must be replaced by a hydroxyl group and the resulting thio-alkanoic ester must be saponified.

When the parameter $n$ is less than 2, the substitution of the halogen atom by a hydroxyl group and the saponification can be carried out simultaneously in a single step by treating the thioether with an alkaline reagent such as sodium or potassium hydroxide. These bases are used in stoichiometric proportion to the ester and halide groups, and by operating at a temperature of about 120°C, a transformation rate greater than 90% is obtained at the end of about 4 to 5 hours. The reaction mass is sufficiently fluid to render the addition of a solvent unnecessary. Moreover, when the medium contains only a small amount of water, it is not necessary to carry out the reaction under pressure.

When $n$ is greater than or equal to 2, the substitution of the halogen atom by the hydroxyl group is carried out by using an alkaline salt of carboxylic acid and the process is terminated by saponifying the thio-alkanoic ester. This substitution is analogous to the one described in French Pat. No. 1,477,048 of Apr. 21, 1966 and the halide formed is separated by filtration before the saponification.

When the preparation is carried out with allyl ethers corresponding to formula (III), free mercapto-alkanoic acids are preferably used. The products according to formula (I) are then obtained directly at the end of several hours, by simply heating the reaction mixture at a temperature between 25° and 150°C, and preferably between 100° and 130°C.

The allyl ethers corresponding to formula (III) can be obtained:

a. by reacting allyl-glycidyl ether with compounds corresponding to the formula RX—(AO)$_m$—H, in which $m$ has a statistical average value between 0 and 10 inclusive and R, X and A have the significances hereinbefore assigned thereto; or b. by reacting glycidyl ethers corresponding to formula (II) with allyl alcohol.

Suitable catalysts for use in these two reactions include alkaline metals, alkaline hydroxides, alkaline alcoholates, alkaline mercaptides and tertiary amines. Acid catalysts, such as boron trifluoride, stannic chloride, and antimony pentachloride can also be used.

In order to prepare these chemical compounds corresponding to formula (I) in which X' represents a sulfoxide group, the corresponding compound in which X' represents a thioether group is first prepared, and then oxidized by adding hydrogen peroxide in the presence of a carboxylic acid, such as acetic acid. Because of the difficulty involved in the elimination of the said carboxylic acid, it is preferred to use it in a small quantity, for example, about 1 to 2% by weight as compared to the dry extract of the preparation. This oxidation is carried out at a temperature between 0° and 50°C and preferably between 30° and 35°C.

In order to prepare those chemical compounds corresponding to formula (I) in which X' represents an oxygen atom, polyetheralcohol alcoholates corresponding to the formula:

(IV)

wherein R, X, A, A'', A''', m and n have the above meanings and wherein M represents an alkali metal, such as sodium, are reacted with a haloalkane carboxylic salt corresponding to the formula:

$$Y\text{---}\underset{\underset{R'}{|}}{CH}\text{---}COOM' \qquad (V)$$

in which
R' has the meaning given above,
M' represents an alkaline metal and
Y represents a halogen atom, preferably chlorine or bromine.

When in the course of this process, it is desired to obtain as an intermediate glycerol ether corresponding to the formula:

$$RX\text{---}(AO)_m\text{---}[C_2H_3O(CH_2Z)]_n\text{---}CH_2CHOH\text{---}CH_2OH \qquad (VI)$$

wherein R, X, A, m and n have the meanings given above and wherein Z represents a halogen atom, an alternative process can be adopted by exploiting the reactivity of the acid function of the haloalkane carboxylic acids. The above reaction can thus be carried out directly by reacting a haloalkane carboxylic acid corresponding to the formula:

$$Y\text{---}\underset{\underset{R'}{|}}{CH}\text{---}COOH \qquad (VII)$$

wherein Y and R' have the meanings given above with a glycidyl ether corresponding to the formula:

$$RX\text{---}(AO)_m\text{---}[C_2H_3O\text{---}(CH_2Z)]_n\text{---}CH_2\text{---}CH\underset{\underset{O}{\diagdown\diagup}}{\text{---}}CH_2 \qquad (VIII)$$

wherein R, A, Z, m and n have the meanings given above and then treating the resulting product with an alkaline metal hydroxide so as to form "in situ" the alkaline salt of a haloalkane carboxylic acid and the alcoholates of the glycerol ethers of formula VI.

The resulting carboxylic acid polyether can be separated from the alkaline salt by using an aqueous solution of a strong mineral acid such as sulfuric acid, and is thus purified.

Finally, the halogen atoms Z are replaced by hydroxyl groups.

In the first step of this process it is preferred to utilize a quantity of haloalkanoic acid from 10 to 100% in excess of the stoichiometric quantity. For the final step, a technique is used which is analogous to the one described above for preparing compounds, having thioether bonds.

Compounds of this invention which illustrate the compounds of formula I and its salts are:

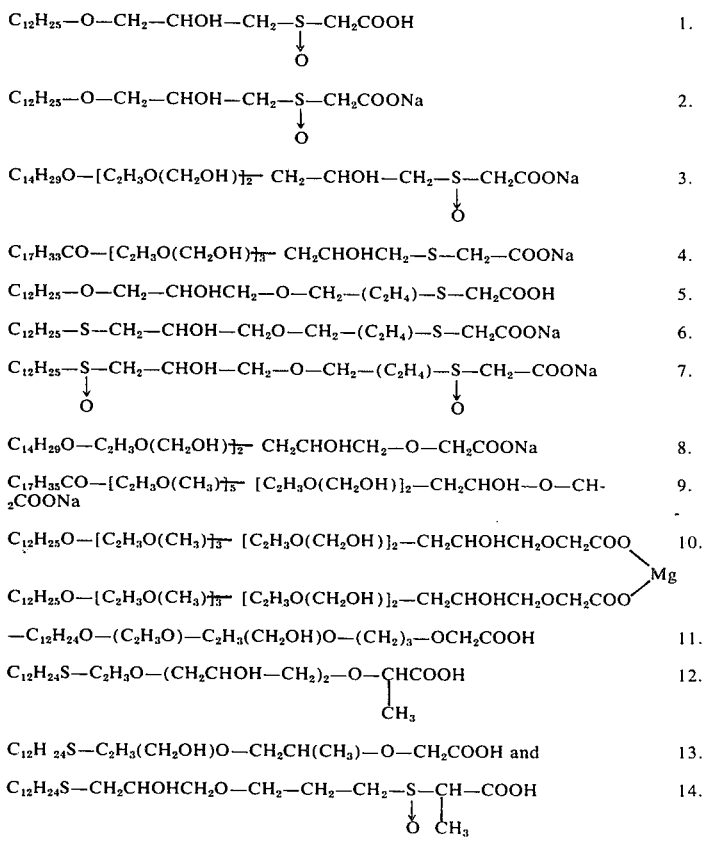

Among the alkyl-aryl groups which can be represented by R in formula I are p-octyl-phenyl, p-nonyl-phenyl, p-dodecyl-phenyl and p-hexadecyl-phenyl.

The products comprising these radicals can be obtained by processes using alkyl-phenols as starting materials. These alkyl-phenols are usually complex mixtures resulting from the alkylation of phenol with hydrocarbons such as diisobutylene, tripropylene, tetrapropylene, or hexadecene.

In order that the invention can be better understood, several methods of preparing compounds corresponding to formula (I) and several examples showing how these compounds can be used in the cosmetic field will now be described:

EXAMPLE 1

Preparation of the compound corresponding to the formula:

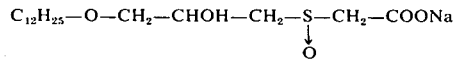

3.5 ml of triethylamine are added to 120g (1 mole) of ethyl thioglycolate under a nitrogen atmosphere. The mixture is brought to 100°C and 242g (1 mole) of distilled dodecylglycidyl ether are added drop by drop. Heating is continued for about three hours. The reaction is then practically complete. The excess ethyl thioglycolate is then eliminated under vacuum.

The ester thus obtained is then poured into 200 cc of acetic acid and 1 mole of hydrogen peroxide at 130 volumes (50% diluted with acetic acid) is then added drop by drop. The reaction is exothermic and the temperature is kept between 30° and 35°C.

After resting overnight at room temperature, no more free peroxides remain. The mixture is then heated under vacuum to eliminate the acetic acid. On cooling the sulfoxide crystallizes out.

The product is redissolved in 200 to 250 cc of $CH_3OH$ and 100 g of 40% NaOH and the sodium soap is precipitated with acetone. The result is an odorless whie powder.

EXAMPLE 2

Preparation of the compound corresponding to the formula:

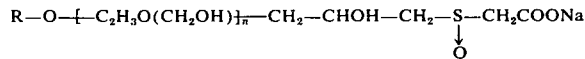

wherein R represents an aliphatic radical containing 12 to 14 carbon atoms and $n$ has a statistical average value of 0.5.

1.6 ml of a boron fluoride acetic acid complex are added to 396g (2 moles) of a mixture of fatty alcohols consisting essentially of dodecanol and tetradecanol. 277g of epichlorohydrin are then added drop by drop, at 75° to 80°C. When the reaction is complete the product is poured into 675g of tertiobutyl alcohol and 300 g of 40% NaOH are added. This mixture is heated for an hour at 75°C. After adding the quantity of water required to dissolve the salt thus formed, salting out yields the epoxide in tertiobutyl alcohol.

300g (1 mole) of the epoxide obtained by distilling the tertiobutyl alcohol are added, drop by drop, at 105° to 115°C, under a nitrogen atmosphere, to 132g (1.1 moles) of ethyl thioglycolate and 4.5 cc of triethylamine. This temperature is maintained for 3 hours. The reaction is then complete. The excess ethyl thioglycolate is then eliminated by heating under a vacuum.

The remaining chlorinated compound is hydrolyzed in a reactor provided with powerful agitating means. 150g (1.5 moles) of 40% NaOH are added to 420g (1 mole) of the resulting ester. The liberated alcohol, plus part of the water introduced, is distilled until a temperature of 120° to 125°C is attained. This temperature is maintained for 4.5 hours. The percentage of hydrolysis is then of the order of 95%. The result is a soap in the form of a stiff paste containing about 80% active material.

In order to obtain the corresponding sulfoxide, this soap is redissolved in 250 cc of water so as to render it sufficiently fluid to oxidize. The thioether is then oxidized with hydrogen peroxide at 130 volumes in stoichiometric proportions in the presence of a catalyst consisting of 1.5 cc of acetic acid per 100g of active materials.

The resulting product is a white cream containing about 50% of the active components.

EXAMPLE 3

Preparation of the compound corresponding to the formula:

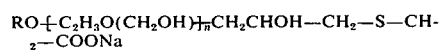

wherein R represents an oleyl radical and $n$ has a statistical average value of 3.

An epoxide is prepared from the compound obtained by reacting 4 moles of epichlorohydrin and oleic alcohol, according to the method indicated in Example 2. 240g of the epoxide produced in this manner are added drop by drop to 53g of ethyl thioglycolate and 2 cc of triethylamine at 110°C under nitrogen atmosphere. A quantitative reaction is obtained at the end of 5 hours.

285 g of the chlorinated ester previously obtained are added in 30 minutes, under a nitrogen atmosphere, at 180°C, to 115g of potassium acetate in 285g of dipropylene glycol. Heating is continued for four hours. The resulting salt is filtered at 100°C and rinsed with dipropylene glycol. Distillation under a pressure of 15 mm of mercury up to 190°C follows.

The residue is redissolved in 250 cc of absolute alcohol and 750 mg of $CH_3ONa$. After leaving it overnight at room temperature, the resulting ethyl acetate and alcohol are distilled, ending up under vacuum at 180°C.

The product is again dissolved in a little alcohol and the ester is saponified with a stoichiometric quantity of 40% sodium hydroxide. Distillation of the alcohol leaves a paste which is soluble in pure water and in concentrated aqueous sodium hydroxide solutions. Aqueous solutions of this product are foam-forming.

The corresponding magnesium salt obtained by double decomposition between the sodium salt and magnesium chloride in an alcoholic medium is perfectly soluble in water.

EXAMPLE 4

Preparation of the compound corresponding to the formula:

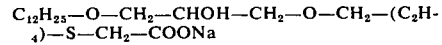

The reaction consists in adding thioglycolic acid to allyl ether and 2-hydroxy-3-lauryloxy propyl. The latter compound is prepared by condensing lauryl alcohol on allyl-glycidyl ether in the presence of sodium methylate in the following manner:

115g of allyl glycidyl ether are added, drop by drop, in 20 minutes, to 186g of aluryl alcohol and 1.2g of sodium methylate, which have been heated to 120° to 140°C. The mixture is then heated to 160°C for 4 tion. The organic phase is dried on sodium sulfate, and filtered. The tertiobutyl alcohol is distilled off. The yield is an epoxide which titration indicates to comprise 1.62 meq/g of oxirane groups.

This epoxide is heated for 6 hours at a temperature between 120° and 160°C. 42g of sodium hydroxide flakes are added at a temperature of 60°C and heated 5 hours at 60° to 80°C. 76g of sodium hydroxide flakes and 89g of monochloroacetic acid are each divided into three factions and added alternately to the mixture.

This mixture is then acidified with 41.5 cc of sulfuric acid, while adding 800 cc of water and heating and stirring for an hour in a water bath. The carboxylic acid salts out prefectly, and is separated and vacuum dried.

The corresponding sodium salt is prepared by adding to this salt in an alcoholic medium as much 40% sodium hydroxide as is necessary to salify the carboxylic function and hydrolyze the remaining chlorine. The mixture is then heated at reflux for 10 minutes, the alcohol distilled off. The mixture is heated to 125°C for four and a half hours, as in Example 2.

EXAMPLE 9

Preparation of the compound corresponding to the formula:

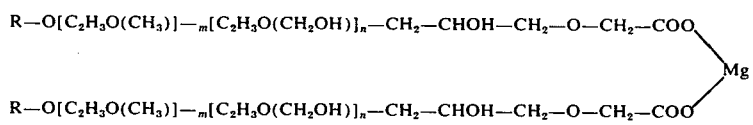

wherein R, m and n have the same meanings as in the preceding Example.

This compound is prepared from the sodium salt obtained as set forth above. 0.2 mole of this salt is dissolved in 50 cc of water and 50 cc of alcohol. At 60°, 40 gr of $MgCl_2$ (100% excess), dissolved in 100 cc of water, are added. The mixture is heated at 70°C for an hour and a half and then poured into 700 to 800 cc of water which has first been heated to 90°C.

This aqueous phase is drawn off, and drying yields the magnesium salt, which takes the form of a brown paste. The percentage of magnesium in the product and in the mother liquor is about 80%. This product can be used as an emulsifier.

EXAMPLE 10

Preparation of the compound corresponding to the formula:

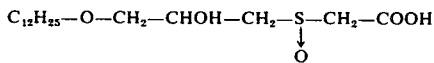

The compound prepared in accordance with Example 1 is neutralized by the addition thereto of HCl. The resulting neutralization product having a pH of 3.3 contains 75 percent of the above free acid. This same procedure can be employed using, alternatively, other strong acids such as sulfuric acid, in amounts sufficient that the neutralization product has a pH ranging between 3.3–4.

EXAMPLE 11

Preparation of the compound corresponding to the formula:

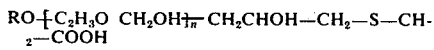

wherein R is oleyl and n has a statistical average value of 3.

19 grams (0.035 mole) of the sodium salt prepared in Example 3 having a base index of 1.77 meq/g corresponding to molecular weight of 565, are added to 19 g of water. The resulting mixture is heated to 40°C thereby completely dissolving the said sodium salt. To the resulting solution 1cc of 36N sulfuric acid is added (0.036 equivalent) and the mixture is heated to boiling. To facilitate salting out the acid a few drops of n-butanol are added and the aqueous phase is then removed. The remainder is then dried under a vacuum yielding a light yellow paste dispersible in water and having a base index of O.

EXAMPLE 12

Preparation of the salt of 2-amino-2 methyl propanol and the acid of Example 10.

2 g of the acid prepared in accordance with Example 10 were dissolved at 40°C in 8 grams of isopropanol. To the resulting solution there is added 0.56 g (5.92 meq.) of 2-amino-2-methyl propanol. The isopropanol solvent is then evaporated thereby yielding an amorphous white residue having a base index of 2.25 meq/g (Theory —2.34 meq/g) and an acid index of 2.30 meq/g (Theory —2.34 meq/g). This compound is soluble in permuted water at a temperature ranging from ambient to the boil, at least in a quantity of 1%.

EXAMPLE 13

Preparation of the salt of triethanolamine and the acid of Example 10.

2g of the acid prepared in accordance with Example 10 were dissolved at 40°C in 8 grams of isopropanol. To the resulting solution there is added 0.84g (5.92 meq) of triethanolamine. The resulting mixture is evaporated to dryness, yielding an amorphous white residue having a base index of 1.92 meq/g (Theory —2.28 meq/g) and an acid index of 2.02 meq/g (Theory —2.28 meq/g). This compound is soluble in permuted water at a temperature ranging from ambient to the boil, at least in a quantity of 1%.

EXAMPLE 14

Preparation of the salt of 2-amino-2-methyl-1, 3-propanediol and the acid of Example 10.

2g of the acid prepared in accordance with Example 10 were dissolved at 40°C in 8 grams of isopropanol. To the resulting solution there is added 0.66g (5.92 meq) of 2-amino-2-methyl-1, 3- propanediol. The resulting mixture is evaporated to dryness, yielding an amorphous white residue having a base index of 2.14 meq/g (Theory —2.26 meq/g) and an acid index of 2.14 meq/g (Theory —2.26 meq/g). This compound is soluble in permuted water at a temperature ranging from ambient to the boil, at least in a quantity of 1%.

hours. Distillation of the crude product obtained in this manner separates the allylether and the 2-hydroxy-3-lauryloxy propyl. This is distilled at 150° to 170°C under a pressure of 1 mm of mercury. 60g (0.2 mole) of ethylene derivative and 10g (0.2 mole) of thiogylcolic acid are mixed and heated to 100°C for 8 or 9 hours. About 90% of the mixture reacts.

The acid index indicates that the product is partially esterified. It is first neutralized and then saponified with a stoichiometric quantity of 40% NaOH in the presence of alcohol. After distillation of the alcohol, the yield is an almost colorless wax, which is soluble in water.

EXAMPLE 5

Preparation of the compound corresponding to the formula:

$$C_{12}H_{25}-S-CH_2-CHOH-CH_2-O-CH_2-(C_2H_4)-S-CH_2-COONa$$

As in Example 4, the product is prepared by adding thiogylcolic acid to the corresponding ethylene derivative. This ethylene derivative is prepared by adding lauryl mercaptan, drop by drop, at 100° to 110°C to an excess (200%) of allyl glycidyl ether while bubbling in notrogen, and in the presence of triethylamine, which constitutes 0.5% of the reaction mass. This addition takes thirty minutes. The reaction is almost instantaneous.

The excess allyl glycidyl ether is eliminated. Then the desired ethylene derivative is distilled at 185°C under 0.5 mm of mercury. A stoichiometric quantity (7.2g) of thiogylcolic acid is added drop by drop, to 28g of the resulting compound. After this addition, the mixture is heated for 5 minutes at 100°C. The acid which has not reacted is eliminated under vacuum. On cooling, the condensation product crystallizes and is then rinsed in petroleum ether. An attractive white powder results.

The sodium soap is obtained by neutralizing this powder with 50% sodium hydroxide in an alcoholic medium and precipiation with acetone.

EXAMPLE 6

Preparation of the compound corresponding to the formula:

$$C_{12}H_{25}-S-CH_2-CHOH-CH_2-O-CH_2-(C_2H_4)-S-CH_2-COONa$$
$$\downarrow \qquad\qquad\qquad\qquad\qquad\qquad\qquad \downarrow$$
$$O \qquad\qquad\qquad\qquad\qquad\qquad\qquad O$$

In order to prepare the disulfoxide, 12 g of the product obtained in acid form in Example 5, are dissolved by heating the same in 5 cc of acetic acid. 5.2 cc of $H_2O_2$ are added drop by drop at the rate of 11.2 moles per liter. The temperature is maintained between 30° and 40°C. After a night at room temperature no more peroxides remain. The acetic acid is distilled off, the remainder neutralized with 50% NaOH in alcohol and precipitation caused by adding acetone.

This yields the desired product in the form of a white powder which dissolves readily in water.

EXAMPLE 7

Preparation of the compound corresponding to the formula:

$$RO-[C_2H_3O(CH_2OH)]_n-CH_2CHOH-CH_2-O-CH_2-COONa$$

wherein R represents an aliphatic radical containing 12 to 14 carbon atoms and $n$ has a statistical average value of 0.5.

400g (1.33 moles) of the expoxide prepared as in Example 2 are added over thirty minutes at 120°C to 151g of monochloroacetic acid in the presence of 11 cc of triethylamine. The mixture is then heated for three hours at 150°C. After cooling to 60°C, 127.5 g of sodium hydroxide flakes are added. The reaction is exothermic. This temperature is maintained until all the sodium hydroxide has reacted. 84g of sodium hydroxide flakes and 101g of monocloroacetic acid are each divided into three parts and added alternately.

The mixture is introduced into 1500 cc of water and 400g of sulfuric acid at half-normal strength are added. On heating to 100°C the acid salts out. 528g of the resulting acid are redissolved in 150g of alcohol at 96°C and sufficient 40% sodium hydroxide aqueous solution is added to neutralize and hydrolyze the organic chlorine. The alcohol and part of the water are distilled off until a temperature of 120°C is reached. This temperature is maintained for 4 hours and the hydrolysis is 96% complete.

On cooling, the yield is a hard product, which can be molded, but is a little fragile.

EXAMPLE 8

Preparation of the compound corresponding to the formula:

$$R-O-[C_2H_3O(CH_3)]_m[C_2H_3O(CH_2OH)]_n-CH_2-CH\ OH-CH_2O-CH_2-COONa$$

wherein R represents a stearyl radical, and $m$ and $n$ have statistical average values of 5.25 and 1 respectively.

52 grams (0.55 mole) of monochloroacetic acid and 7 cc of triethylamine are heared to 100° to 110°C and in an hour and 30 minutes, 308gr of the epoxide corresponding to the following formula are then added:

$$R-O-[C_2H_3O(CH_3)]_m \qquad -[C_2H_3O(CH_2OH)]_n$$
$$-CH_2 -CH -CH_2$$

wherein R is stearyl.

This epoxide is prepared in the following manner.

6.25 moles of a boron fluoride acetic acid complex are added to one mole of molten stearyl alcohol which has been dehydrated by heating under a 15 mm pressure in a boiling water bath. 5.25 moles of propylene oxide are then added drop by drop. The reaction is exothermic and takes place at 75° to 80°C. The addition of the propylene oxide takes frm 1 hour and 30 minutes to 1 hour and 45 minutes.

The epichlorhydrin is condensed immediately after oxypropylenation, at 75° to 80°C over a period of 30 minutes. The resulting polychlorinated polyether has a hydroxyl index of 90.

An equal weight of tertiobutyl alcohol is added to the polychlorinated polyether and in ten minutes, 150g of 40% sodium hydroxide are also added. The resulting mixture is heated to 65° for 30 minutes. The minimum amount of water required to solubilize the resulting salt is added and the aqueous phase separated by decanta-

EXAMPLE 15

Preparation of the salt of 2-amino-2-methyl propanol and the acid of Example 11.

2.45 grams (3.18 meq) of the acid prepared in accordance with Example 11 and 0.305 gram of 2-amino-2-methyl propanol are dissolved in 6.4 grams of water. The resulting solution is heated on a water bath for a period of about 30 minutes, yielding the above compound in viscous paste form having a base index of 1.22 meq/g and an acid index of 1.17 meq/g. This compound is soluble in permuted water at a tempeature ranging from ambient to the boil, at least in a quantity of 1%.

EXAMPLE 16

Preparation of the salt of 2-amino-2-methyl-1,3- propanediol and the acid of Example 11.

2.35 g (3.04 meq) of the acid prepared in accordance with Example 11 and 0.44g of 2-amino-2-methyl-1,3propanediol are dissolved in 5.7 grams of water. The resulting solution is heated on a water bath for 30 minutes, yielding the above compound in viscous paste form having a base index of 1.28 meq/g and an acid index of 1.21 meq/g. This compound is soluble in permuted water at a temperature ranging from ambient to the boil, at least in a quantity of 1%.

EXAMPLE 17

Preparation of the salt of triethanolamine and the acid of Example 11. 3.74 grams of the acid prepared in accordance with Example 11 and 0.68 g of triethanolamine are dissolved in 7.2 grams of water. The resulting solution is heated on a water bath for 30 minutes, yielding the above compound in paste form having a base index of 1.46 meq/g and an acid index of 1.48 meq/g. This compound is soluble in permuted water at a temperature ranging from ambient to the boil, at least in a quantity of 1%.

EXAMPLE 18

The following composition was prepared:

| | |
|---|---|
| $C_{12}H_{25}OCH_2-CHOH-CH_2-\underset{\downarrow}{S}-CH_2-COONa$ | 10 g |
| O | |
| Lauryl diethanolamide | 2 g |
| Soybean lecithin | 0.5 g |
| 2-butoxy ethanol | 0.5 g |
| Hydroxypropylmethylcellulose | 0.2 g |
| Water, q.s.p. | 100 g |

The pH of the composition is at least equal to 7. It is limpid, has valuable forming properties, and can be used in a quantity of about 20 cc as a shampoo for the hair.

EXAMPLE 19

The following composition was prepared:

| | |
|---|---|
| $C_{12}H_{25}OCH_2-CHOH-CH_2-\underset{\downarrow}{S}-CH_2-COONa$ | 5 g |
| O | |
| Sodium salt of sulfuric ester of lauryl alcohol polyethoxylated with 2 moles of ethylene oxide | 5 g |
| Lauryl diethanolamide | 2.5 g |
| Hydroxypropylmethylcellulose | 0.3 g |
| Water, q.s.p. | 100 g |

The composition has a pH of 7, is limpid, and has valuable foaming properties. It can be used, in a quantity of about 20 cc, as a shampoo for the hair.

EXAMPLE 20

The following composition was prepared:

| | |
|---|---|
| $C_{12}H_{25}OCH_2CHOH-CH_2-OCH_2-(C_2H_4)-S-CH_2-COONa$ | 15 g |
| Lauryl diethanolamide | 2.5 g |
| Soybean lecithin | 0.5 g |
| 2-methoxy ethanol | 0.5 g |
| Hydroxypropylmethylcellulose | 0.25 g |
| Water, q.s.p. | 100 g |

The composition has a pH of 7, is limpid, and has valuable foaming properties. About 20 cc serve as an excellent shampoo for the hair.

EXAMPLE 21

The following composition was prepared:

| | |
|---|---|
| $C_{12}H_{25}OCH_2CHOH-CH_2-OCH_2-(C_2H_4)-S-CH_2-COONa$ | 6 g |
| Sodium salt of sulfuric ester of lauryl alcohol polyethoxylated with two moles of ethylene oxide | 5 g |
| Lauryl diethanolamide | 2.5 g |
| Acetylated lanolin | 0.5 g |
| Water, q.s.p. | 100 g |

The composition has a pH equal to 7, is limpid, and has valuable foaming properties. 20 cc make an excellent shampoo for the hair.

EXAMPLE 22

The following composition was prepared:

$$RO-[C_2H_3O(CH_2OH)]_n-CH_2-CHOH-CH_2-O\underset{COONa}{CH_2} \qquad 15\ g$$

wherein R represents an alkyl radical containing 12 to 14 carbon atoms and n has a statistical average value of 0.5.

| | |
|---|---|
| Acetylated lanolin | 1 g |
| Hydroxypropylmethylcellulose | 0.25 g |
| Water, q.s.p. | 100 g |

The composition has a pH of 7, is limpid, and has valuable foaming properties. 20 cc serve as an excellent shampoo for the hair.

EXAMPLE 23

The following composition was prepared:

$$RO-[C_2H_3O(CH_2OH)]_n-CH_2-CHOH-CH_2-O\underset{COONa}{CH_2} \qquad 15\ g$$

wherein R represents an alkyl radical containing 12 to 14 carbon atoms, and $n$ has a statistical average value of 0.5.

| | |
|---|---|
| Sodium salt of sulfuric ester of lauryl alcohol polyethoxylated with 2 moles of ethylene oxide | 5 g |
| Lauryl diethanolamide | 2 g |
| Hydroxypropylmethylcellulose | 0.2 g |
| Water, q.s.p. | 100 g |

The composition has a pH of 7, is limpid, and has valuable foaming properties. 20 cc serve as an excellent shampoo for the hair.

EXAMPLE 24

The following hair dye composition was prepared:

| | |
|---|---|
| Bis-methyl [1,5($\gamma$-trimethyl-ammonium)-propylaminoanthraquinone] sulfate | 1.65 g |
| $C_{12}H_{25}$—OCH$_2$—CHOH—CH$_2$—S—CH$_2$COONa<br>$\qquad\qquad\qquad\qquad\qquad\qquad\downarrow$<br>$\qquad\qquad\qquad\qquad\qquad\qquad$ O | 2.00 g |
| 20% solution of isooctylphenylpolyethoxyethanol | 4.60 g |
| Monoethanolamine, q.s.p. | pH 8 |
| Water, q.s.p. | 100 g |

1.65g of bis-methyl-[1,5 ($\gamma$-trimethyl-ammonium)-propylaminoanthraquinone] sulfate are dissolved in the minimum possible amount of water and adjusted to pH 7 with monoethanolamine. Into this solution 100 g/liter of a solution of

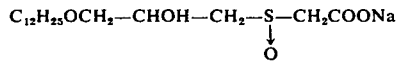

is poured drop by drop from a burette. Beginning with the first drop, a deep red product begins to precipiate. The course of this precipitation is tested by drops on filter paper and it was found that the precipitation increases in proportion to the quantity of the product corresponding to the above formula introduced, while the solution clears. The maximum precipitation occurs when 20 cc of the surface active solution were used. The solution becomes colorless. A slight excess of the product according to the above formula produces a tendency to redissolve the precipitate. The resulting product was dissolved in the minimum quantity of a 20% solution of isooctylphenylpolyethoxyethanol. The course of this redissolution was followed by depositing drops of the solution on filter paper using a burette. It requires 23 cc of a 20% isooctylphenylpolyethoxyethanol solution to completely redissolve this product. The pH was adjusted to 8 with monoethanolamine, the solution was increased to 100g, and no reprecipitation was noted. It was found that this product contained about 2.2 molecules of the product corresponding to the formula:

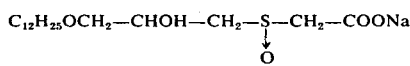

for each molecule of dye. (This is very close to a stoichiometric proportion, since bis-methyl[1,5($\gamma$-trimethyl-ammonium)-propylaminoanthraquinone] sulfate is dibasic).

This composition was applied to chestnut hair. The product was a good foam former. It is left on the hair for 15 minutes. The hais is then washed and rinsed. A strong mahogany shade results.

EXAMPLE 25

Following the method outlined in Example 24, an anion-cation product was prepared, utilizing bis-methyl [1,5($\gamma$-trimethyl-ammonium)-propylamino-anthraquinone] sulfate. In this manner the following composition is prepared:

| | |
|---|---|
| Bis-methyl [1,5($\gamma$-trimethyl-ammonium)-propylaminoanthraquinone] sulfate | 1.65 g |
| R—[OC$_2$H$_3$(CH$_2$OH)]$_n$—OCH$_2$—CHOH—CH$_2$—S—CH$_2$COONa<br>$\qquad\qquad\qquad\qquad\qquad\qquad\qquad\qquad\qquad\qquad\downarrow$<br>$\qquad\qquad\qquad\qquad\qquad\qquad\qquad\qquad\qquad\qquad$ O<br>wherein R represents an aliphatic radical containing 12 to 14 carbon atoms and $n = 0.5$ | 2.30 g |
| 20% solution of isoctylphenylpolyethoxyethanol | 4.30 g |
| Monoethanolamine, q.s.p. | pH 8 |
| Water, q.s.p. | 100 g |

In this example, the anion is present in an excess of 8 to 10% over stoichiometric proportions. Applied to hair as in Example 24, this composition imparts thereto a very beautiful mahogany color.

EXAMPLE 26

The following composition was prepared:

| | |
|---|---|
| 4-N-methylamino-3-nitro-1-N-$\beta$-aminoethyl-amino benzene | 0.29 g |
| R—[OC$_2$H$_3$(CH$_2$OH)]$_n$— OCH$_2$—CHOH—CH$_2$—S—CH$_2$COONa<br>wherein R represents oleyl and $n = 1$ | 0.72 g |
| 20% isooctylphenylpolyethoxyethanol solution | 1.60 g |
| Monoethanolamine q.s.p. | pH 8 |
| Water, q.s.p. | 100 g |

The resulting composition was in the form of a partially soluble paste, even though there was not a complete precipitation resulting in a colorless solution. But the quantity of anion producing the maximum precipitation was carefully determined from the point at which a slight excess of anion redissolves the product. The excess of anion over stoichiometric proportions is 10%. The product foams well.

The composition was applied to chestnut hair and left thereon for 15 minutes, after which the hair was rinsed and washed. A deep violine shade results.

EXAMPLE 27

The following composition was prepared:

| | |
|---|---|
| 4-N-methylamino-3-nitro-1-N-β-aminoethylamino benzene | 0.29 g |
| R[OC$_2$H$_3$(CH$_2$OH)]$_{\overline{n}}$ OCH$_2$—CHOH—CH$_2$—S—CH$_2$—COONa wherein R is oleyl and n = 1 | 0.53 g |
| 20% isooctylphenylpolyethoxyethanol solution | 1.60 g |
| Monoethanolamine, q.s.p. | pH 8 |
| Water, q.s.p. | 100 g |

In preparing the active product it is difficult to detect any precipitation since this product is very soluble. A stoichiometric quantity of anion was therefore used.

When applied to hair as in Example 26 this composition also produces a violine shade, but one a little less red than in the preceding example.

EXAMPLE 28

The following composition was prepared following the same procedure as in Example 24:

| | |
|---|---|
| Bis-methyl [1,5(γ-trimethylammonium)-propylaminoanthraquinone] sulfate | 1.65 g |
| R—[OC$_2$H$_3$(CH$_2$OH)]$_n$ OCH$_2$—CHOH—CH$_2$—S—CH$_2$—COONa wherein R represents an aliphatic radical containing from 12 to 14 carbon atoms and n = 0.5 | 2.6 g |
| 20% isooctylphenylpolyethoxyethanol solution | 3.20 g |
| Monoethanolamine, q.s.p. | pH 8 |
| Water, q.s.p. | 100 g |

In this case the anion is in 20% excess of stoichiometric proportions. The composition is very foam-forming.

It was applied to chestnut hair and left thereon for fiteen minutes, after which the hair was rinsed and shampooed. The result was a very strong mahogany color.

EXAMPLE 29

A hair shampoo conposition was prepared by admixing the following components:

| | |
|---|---|
| Acid of Example 10 | 6 g |
| Lauryl alcohol oxyethylenated with 12 moles of ethylene oxide | 6 g |
| Lauryl diethanolamide | 2 g |
| Water, q.s.p. | 100 g |
| pH | 3.3 |

This composition has excellent foaming characteristics and when used as a shampoo for hair makes the same very soft to the touch.

EXAMPLE 30

A hair shampoo composition was prepared by admixing the following components:

| | |
|---|---|
| Salt of Example 15 | 15 g |
| Lauryl isopropanolamide | 1 g |
| Etherified cellulose | 0.1 g |
| Water, q.s.p. | 100 g |
| pH | 7.5 |

The above composition exhibited excellent foaming properties and imparted to the hair characteristics comparable to those achieved when using the composition of Example 29. This composition is limpid.

EXAMPLE 31

A hair shampoo composition was prepared by admixing the following components:

| | |
|---|---|
| Salt of Example 13 | 8 g |
| C$_{12}$–C$_{14}$ alkyl sulfate of triethanolamine | 5 g |
| Lauryl monoethanolamide | 1 g |
| Water, q.s.p. | 100 g |
| pH | 8 |

This composition also exhibited highly desirable foaming properties and when applied to hair imparted thereto characteristics equally comparable to those achieved with the use of the shampoo compositions of Examples 29 and 30, and it is limpid.

EXAMPLE 32

A hair shampoo composition was prepared by admixing the following components:

| | |
|---|---|
| Acid compound of example 10 | 5 g |
| Lauryl diethanolamide | 1.5 g |
| C$_{12}$–C$_{14}$ alcohol oxyethylenated with 12,5 moles of ethylene oxide | 5 g |
| Acetic acid q.s. pH 4 | |
| Water q.s.p. | 100 g |

This composition has excellent foaming characteristics comparable to those achieved when using the composition of example 29 and is perfectly limpid.

What is claimed is:

1. A cosmetic composition consisting essentially of in an aqueous solution a surface active agent selected from the group consisting of
   a. a surface active agent of the formula $$RX-(AO)_m-(A'O)_n-A''-X'-\underset{\underset{R'}{|}}{C}H-COOH$$

wherein
R is selected from the group consisting of alkyl and alkenyl, each having 8–22 carbon atoms and alkyl phenyl selected from the group consisting of p-octyl phenyl, p-nonyl phenyl, p-dodecyl phenyl and p-hexadecyl phenyl;
X and X' are each selected from the group consisting of oxygen, sulfur and sulfoxide;
A is selected from the group consisting of ethylene, propylene and butylene;

A' is selected from the group consisting of —C$_2$H$_3$(CH$_2$OH)— and —CH$_2$CHOH—CH$_2$—;

A" is selected from the group consisting of —CH$_2$CHOH—CH$_2$—, —CH$_2$CH$_2$CH$_2$— and —CH$_2$CH(CH$_3$), with the proviso that at least one of A' and A" is hydroxyalkylene as set forth in the respective definitions of A' and A" above;

$m$ and $n$ represent numbers having a statistical average value between 0–10 inclusive, with the proviso that $n$ is other than 0 when A" is other than hydroxyalkylene and when $m$ and $n$ are both equal to zero, X' is sulfoxide; and R' is selected from the group consisting of hydrogen and alkyl having from 1–12 carbon atoms, b. the magnesium salt of (a); and
c. the alkanolamine salt of (a), said alkanolamine being selected from the group consisting of 2-amino-2-methyl propanol, triethanolamine and 2-amino-2-methyl-1,3-propanediol, said surface active agent being present in amounts ranging from 0.1 – 20% by weight of said composition.

2. The composition of claim 1 having a pH of 3–10.

3. The composition of claim 1 wherein the surface active agent has the formula

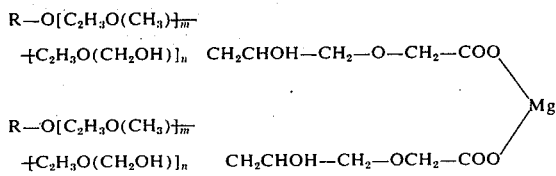

wherein R is stearyl and $m$ and $n$ have a statistical average value of 5.25 and 1 rspectively.

4. The composition of claim 1 wherein the surface active agent has the formula $$C_{12}H_{25}-O-CH_2-CHOH-CH_2-\underset{O}{\overset{\downarrow}{S}}-CH_2-COOH$$

5. The composition of claim 1 wherein the surface active agent has the formula

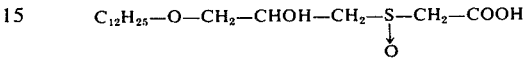
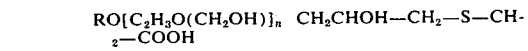

wherein R is alkyl and $n$ has a statistical average value of 3.

* * * * *

UNITED STATES PATENT OFFICE
CERTIFICATE OF CORRECTION

Patent No. 3,959,460        Dated May 25, 1976

Inventor(s) Guy Vanlerberghe and Henri Sebag

It is certified that error appears in the above-identified patent and that said Letters Patent are hereby corrected as shown below:

In the Heading:

Under "United States Patent [19]", "Vanlergerghe et al." should read --Vanlerberghe et al.--

Under [75], "Guy Vanlergerghe" should read --Guy Vanlerberghe--.

Signed and Sealed this

Twenty-sixth Day of October 1976

[SEAL]

Attest:

RUTH C. MASON
*Attesting Officer*

C. MARSHALL DANN
*Commissioner of Patents and Trademarks*